(12) United States Patent
Perez et al.

(10) Patent No.: US 7,216,978 B2
(45) Date of Patent: May 15, 2007

(54) METHOD FOR EVALUATING EYELID MOVEMENT AND CONTACT LENS POSITION

(75) Inventors: Jose L. Perez, Jacksonville, FL (US); Daoud Robert Iskander, Brisbane (AU); Michael Collins, Jollys Lookout (AU)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 0 days.

(21) Appl. No.: 11/148,077

(22) Filed: Jun. 8, 2005

(65) Prior Publication Data
US 2006/0279696 A1    Dec. 14, 2006

(51) Int. Cl.
*G02C 7/02* (2006.01)

(52) U.S. Cl. .................................. 351/177; 351/160 R

(58) Field of Classification Search .............. 351/177, 351/160 R, 247
See application file for complete search history.

(56) References Cited

U.S. PATENT DOCUMENTS

| 5,686,981 A | 11/1997 | Anan et al. |
| 6,076,930 A * | 6/2000 | Malchow et al. ........... 351/247 |
| 2002/0159030 A1 * | 10/2002 | Frey et al. .................. 351/212 |

FOREIGN PATENT DOCUMENTS

| DE | 20212917 | 10/2002 |
| EP | 0949528 | 10/1999 |
| WO | WO 04/021875 A1 | 3/2004 |
| WO | WO 05/015290 | 2/2005 |

OTHER PUBLICATIONS

PCT International Search Report, dated Oct. 4, 2006, for PCT Int'l. Appln. No. PCT/US2006/020700.

* cited by examiner

Primary Examiner—Scott J. Sugarman
Assistant Examiner—Darryl J. Collins
(74) Attorney, Agent, or Firm—Lois A. Gianneschi

(57) ABSTRACT

A method for designing contact lenses is provided in which direct correlation is made between an individual's subjective assessment of the lens' performance with the objective measurement of one or both of on-eye lens position and eyelid movement. The method permits generation of lens designs that have enhanced on-eye stability in less time than conventional design methods.

5 Claims, 3 Drawing Sheets

METHOD FOR EVALUATING EYELID MOVEMENT AND CONTACT LENS POSITION

FIELD OF THE INVENTION

The present invention relates to methods for designing ophthalmic lenses. In particular, the invention provides a method for designing contact lenses by taking into account eyelid movement and on-eye contact lens position. The invention also provides a method for designing a lens customized to an individual.

BACKGROUND OF THE INVENTION

The use of ophthalmic lenses, such as contact lenses, for the correction of ametropia is well known. A number of methods for designing contact lenses also are known. Typically, these methods involve one or more of benchmarking of known designs, developing theoretical target values for control optical parameters, obtaining subjective patient feedback, and using objective testing methods to produce a lens design. One disadvantage of these design methods is that they do not accurately take into account the effect of on-eye movement of the lens or the effect of eyelid movement on lens stability.

Additionally, for correction of certain optical defects, non-spherical corrective characteristics must be designed into one or more surfaces of the contact lens such as cylindrical, bifocal, or multifocal characteristics. However, the design of these lenses is problematic in that the lens must be designed to perform so as to quickly attain and then maintain a specific orientation while on the eye to be effective. Evaluating performance of the lens designs that incorporate non-spherical correction requires many iterations during which the lens is tested on-eye, feedback from the lens wearer is used to optimize the lens design, and the lens is re-tested on-eye, resulting in a lens design and evaluation cycle that is lengthy.

DESCRIPTION OF THE INVENTION AND ITS PREFERRED EMBODIMENTS

Figure 1:
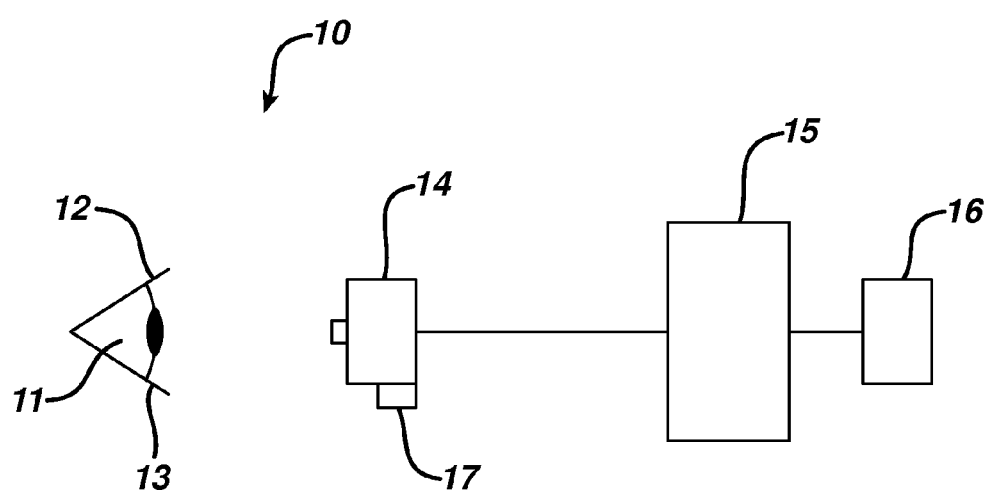
FIG. 1 is a schematic diagram of one embodiment of an apparatus used to carry out the method of the invention.

In the present invention, a method for designing contact lenses, including toric contact lenses, and lenses produced by the method are provided. The method of the invention permits the direct correlation of an individual's subjective assessment of the lens' performance with the objective measurement of one or both of on-eye lens position and eyelid movement. The method permits generation of lens designs that have enhanced on-eye stability in less time than conventional design methods. Additionally, the method may be used to design a lens that is customized to an individual.

In one embodiment, the invention provides a method comprising, consisting essentially of, and consisting of the steps of: a.) placing a contact lens comprising a first design on an individual's eye; b.) recording one or both of the individual's eyelid movement and the contact lens position over an effective period of time; c.) analyzing the recording to evaluate one or both of the individual's eyelid movement and the contact lens position; and d.) modifying the first design using the information obtained in step c.) to provide a second lens having a second design.

The invention may be used to design spherical contact lenses, but may find its greatest utility in the design of non-rotationally symmetric contact lenses including, without limitation, toric and multifocal contact lenses and rotationally symmetric but aspheric contact lenses.

In the first step of the method of the method of the invention, a first contact lens having a first lens design is placed on an individual's eye. The lens may be designed using any conventionally available method for designing contact lenses. For example, the lens may be designed using commercially available software including, without limitation, ZEMAX™, CODE V™, OSLO™, and the like. Typically, the lens will be designed by describing each surface of the lens in mathematical terms. The shape that the described surface may take is limited only by the density of the elements or coefficients used to describe the surface. Preferably, the lens is a lens in which one of the front, or object side, and the back, or eye side, surface is either non-rotationally symmetric or is aspheric.

Once the designing of the first lens is complete, a lens according to the first design is produced by any convenient method. Methods for producing contact lenses are well known and include, without limitation, lathing, molding, or a combination of machining and molding.

Once the lens is placed on-eye, a recording is made of the lens, while on the individual's eye. The recording provides information on one or both of the contact lens' position on-eye as well as the individual's eyelid movement, and its effect on lens position over time. The recording may be carried out using any convenient method and equipment. Preferably, a high speed video camera is used meaning a video camera capable of recording at about 500 frames/sec. or greater. Suitable video cameras are commercially available and include, without limitation, PHANTOM V5™ available from Vision Research, Inc., PHOTRON FASTCAM PCI™ available from Photron, Inc., MOTIONPRO™ 500 available from Redlake MASD, Inc., and the like.

The exact distance of the camera from the eye is not critical and will depend upon the camera lens' focusing power. Preferably, an image of 800×600 pixels of the eye and eyelids is adequate. Also, preferably, the camera is positioned at about 1 to about 2 feet from the lens wearer's eye in a line extending between the center of the lens to the center of the eye. Illumination may be provided by ambient lighting. Alternatively, the camera may be attached to a slit lamp, through an appropriate optical link including, without limitation a mirror, a beam-splitter, or the like. Use of a slit lamp is disadvantageous in that the bright light of the lamp may induce blinking. Thus, as yet another alternative and preferably, an infra-red lamp may be situated to one side of the camera and used to illuminate the eye or infra-red illumination may be incorporated into a slit lamp. The amount of infra-red light used preferably will be proportional to the sampling frequency of the camera used. For example, at 500 frames per second, a 25 Watt bulb with a Wratten 89B filter is sufficient.

The head of the individual preferably is stabilized by any convenient means including, without limitation, by use of a forehead rest, a chin rest, and the like. As an optional step, and whether the head is stabilized or not, marks may be placed on the individual's face so that head movement may be tracked and, subsequently, subtracted from the eyelid movement.

The time period for which the recording is a period effective to gather sufficient data to carry out the analysis desired. The period of time will depend on the memory capacity and sampling rate of the camera used as well as the individual's blink rate. The human blink rate is typically between about 6 to about 15 blinks per minute with each blink lasting about one-quarter of a second. Preferably, the time period is sufficient to record at least five blinks. Because natural blinks, as opposed to those induced by lighting conditions are to be recorded, multiple recording sessions of an individual may be necessary.

Typically, the eyelid and lens movement will be readily visible on the recording. However, in order to facilitate identification of the movement, preferably one or both of the lens and eyelids may be marked with a readily visible mark. The marks may be located at any area of the eyelid, but conveniently and preferably are located about 1 to about 5 mm from the outermost portion of the eyelid, meaning the portion of the eyelid closest to the eye. If the lens is a non-rotationally symmetric lens, such as a toric lens, the lens usually will be manufactured with the orientation marks typically used on such a lens. If these marks are not readily visible, or if additional visibility of the lens is desired, the lens may be marked with any suitable marking material.

In the method of the invention, once the recording is completed, one or both of the eyelid movement and lens position may be analyzed by tracking their movements using software capable of performing a line analysis of the recorded images. Any suitable commercially available software may be used including, without limitation, MAX-TRAQ™, FACELAB™, or the like. The software is installed on any suitable computer including, without limitation, a WINDOWS™-based personal computer such as an IBM THINKPAD™ T40. The camera may be connected to the computer by any convenient link capable of transferring images stored in the camera's memory to the computer which links include, without limitation, a FIREWIRE™ link. Commercially available software may be used to convert the recorded images into the desired format including, without limitation, TIFF files, JPEG files, and the like.

In FIG. 1 is shown device 10 that is useful in carrying out the method of the invention. Device 10 is composed of high speed camera 14 and infra-red light 17 removably attached thereto. Camera 14 is positioned in front of eye 11 and eyelids 12 and 13. Camera 14 is linked to computer 15, which in turn is linked to monitor 16.

Using the computer, the values for one or both of the eyelid movement and lens position are plotted by the tracking software. If additional analysis is desired, a file of data points may be exported in any convenient form, such as in an EXCEL™ spreadsheet.

Figure 2:
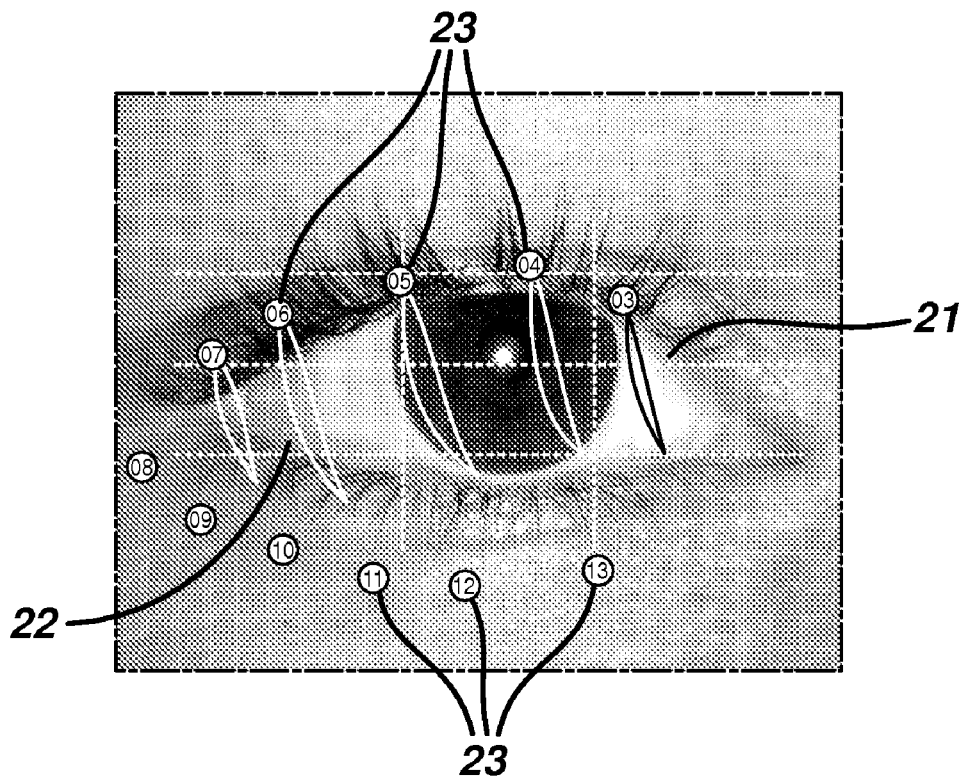
FIG. 2 is a schematic showing a person's eyelids and points for tracking and plotting of the eyelids' movements.
Figure 3:
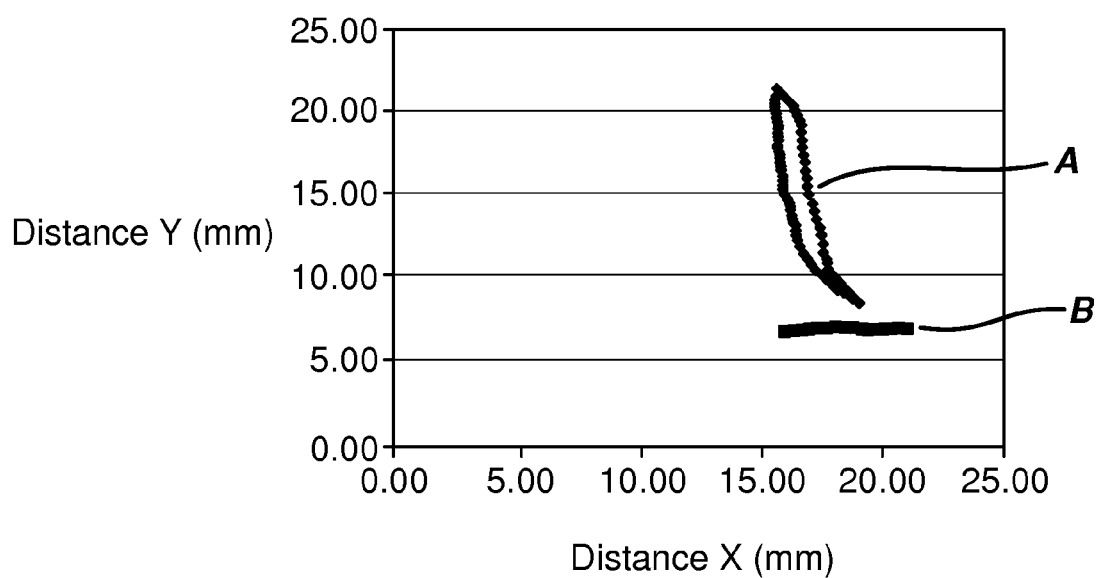
FIG. 3 is a graph depicting a movement profile for an upper and lower eyelid.

In FIG. 2 is shown a view of an eye and its upper eyelid 21 and lower eyelid 22. As shown, multiple points 23 are marked on each of the upper and lower eyelids and plotted. FIG. 3 is a magnified view of an example of a plot A of the movement of a point on an upper eyelid and plot B of a lower eyelid during the course of one blink cycle. The plot was created using MaxTraq data exported into EXCEL and shows that the upper eyelid moves in an up and down direction, but the lower eyelid moves in a lateral direction.

The plotted values may be, and preferably are, visually analyzed and the miscaptured points, or points that do not follow a smooth profile, eliminated by using the information from the surrounding points. The plot may be further smoothed by using any number of mathematical functions including, without limitation, a spline function, polynomial, interpolation or the like through the points. Smoothing reduces or eliminates tremors that are the artifacts of the numerical tracking algorithms used. Once the smoothing is concluded, the eyelid-lens interaction may be quantified by measuring the amount of lens rotation resulting from each blink and the lens rotation and eyelid movement measured are plotted in a time series chart to correlate lens rotation in degrees versus the number of blinks.

In the final step of the method of the invention, the first contact lens design is modified using the information obtained from the eyelid-lens movement analysis. For example, by knowing the manner in which the eyelid edge approaches a stabilization zone of the lens, the stabilization zones may be moved, reshaped, or both until either or both the lens' resting position and the maximum lens stability are obtained while the lens is on-eye. The redesign of the lens may be carried out using commercially available software describing each surface of the lens in mathematical terms. Confirmation of whether the second design achieves the desired performance may be evaluated using the method of the invention.

What is claimed is:

1. A method for designing a contact lens, comprising the steps of: a.) placing a contact lens comprising a first design on an individual's eye; b.) recording one or both of the individual's eyelid movement and the contact lens position over a period of time; c.) analyzing the recording to evaluate one or both of the individual's eyelid movement and the contact lens position; and d.) modifying the first design using the information obtained in step c.) to provide a second lens having a second design.

2. The method of claim 1, wherein step b.) is carried out by recording an individual's eye using a high speed video camera.

3. The method of claim 1, wherein step b.) further comprises illuminating the eye with an infra-red lamp.

4. The method of claim 1, further comprising the step of marking the eyelids, the lens, or the eyelids and the lens.

5. A contact lens provided using the method of claim 1.

* * * * *